June 15, 1954 E. S. BOERNER Plant Pat. 1,285
ROSE PLANT
Filed May 13, 1953
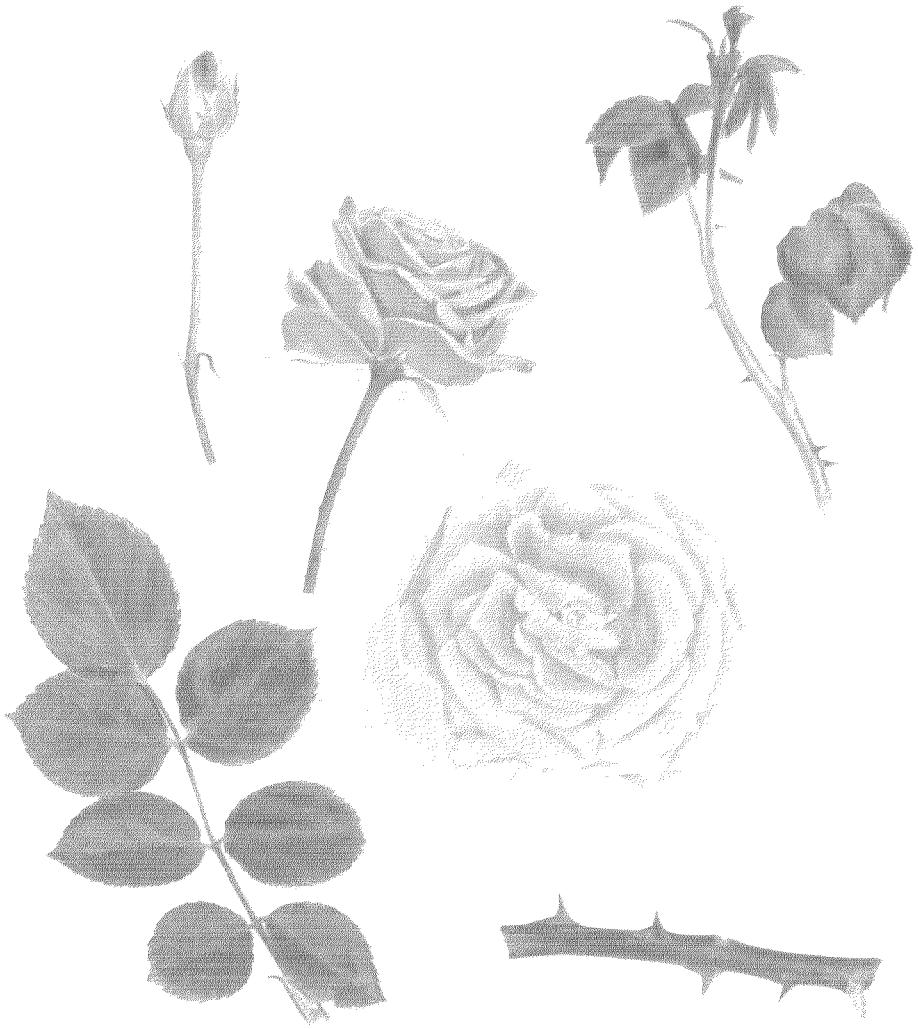
Inventor
E. S. Boerner
By: Robb & Robb
Attorneys Patented June 15, 1954

Plant Pat. 1,285

UNITED STATES PATENT OFFICE 1,285

ROSE PLANT

Eugene S. Boerner, Newark, N. Y., assignor to Jackson & Perkins Company, Newark, N. Y., a corporation of New York Application May 13, 1953, Serial No. 354,903

1 Claim. (Cl. 47—61)

The present invention relates to a new and distinct variety of rose plant of the large-flowered polyantha class, which was originated by me by crossing an unnamed and unpatented peach-colored seedling of "Pinocchio" (Plant Patent No. 484) with the variety "Vogue" (Plant Patent No. 926).

The primary objective in making this cross was to obtain an improvement in the color and general overall plant and blooming habits of the variety "Pinocchio." This objective was fully achieved, and I have produced a new variety of rose plant which is distinguished from its parents, as well as from all other varieties of its class, as evidenced by its following combination of outstanding characteristics:

(1) A type of plant growth like that of the variety "Pinocchio," but having flowers of a new and different color as hereinafter more fully described:

(2) Flowers of the "Pinocchio" type, but of Begonia Rose general color tonality in the half-open flower, and Eosine Pink color with the lower half of the petals suffused with La France Pink in the fully-open flower;

(3) The great floriferousness of its blooms of the type and color aforesaid; and (4) The suitability of the variety for both outdoor planting and greenhouse culture.

Asexual reproduction of my new variety by budding at Newark, New York, and at Pleasanton, California, shows that the foregoing characteristics and distinctions come true to form and are established and transmitted through succeeding propagations.

The accompanying drawing shows specimens of the flowers, foliage and stems of my new variety in different stages of development, and depicted in color as nearly true as it is reasonably possible to make the same in color illustrations of this character.

The following is a detailed description of my new variety, with color terminology in accordance with Ridgway's Color Standards and Nomenclature:

Parentage: Seedling.

*Seed parent.*—An unnamed peach-colored seedling of "Pinocchio."

*Pollen parent.*—"Vogue."

Classification:

*Botanic.*—Large-flowered polyantha.

*Commercial.*—Floribunda.

*Flower*

(Observations made in a greenhouse at Newark, New York, in the late morning in the early part of the month of May.)

Blooming habit: Recurrent—continuous.

Bud:

*Size.*—Medium.

*Form.*—Globular; is not affected by wet or hot weather.

*Color.*—When sepals first divide—Spinel Red, Plate 26. When petals begin to unfurl—Spinel Red, Plate 26, lightly overcast with Spinel Pink, Plate 26. When half blown: inside of petals—Begonia Rose, Plate 1; reverse of petals—Rose Red, Plate 12, lightly overcast with Rose Color, Plate 12.

*Sepals.*—Branched; curl back when petals begin to unfurl. Color: inside—Kildare Green, plate 31; outside—Cress Green, Plate 31.

*Calyx.*—Shape — funnel. Size — small. Aspect—smooth. Odor when rubbed—none. Color—Spinach Green, Plate 5.

*Peduncle.* — Length—short. Aspect—prickly. Color — Courge Green, Plate 17. Strength—erect; slender.

*Opening.*—Opens well; is not affected by adverse weather conditions.

Bloom:

*Size.*—Medium; average size when fully expanded—2½ inches.

*Borne.*—Several together and in pyramidal clusters.

*Stems.*—Long; normal strength.

*Form.*—When first open—cupped. Permanence—retains its form to the end; outer petals curl back.

*Petalage.*—Double (full but open center); number of petals under normal conditions—45 to 50.

*Color.*—Center of flower—Geranium Pink, Plate 1, lightly overcast with Grenadine Pink, Plate 2. Outer petals—Eosine Pink, Plate 1, lightly overcast with Thulite Pink, Plate 26. Base of petals (aiglet)—Sulphur Yellow, Plate 5. Inside of petals—Eosine Pink, Plate 1; lower half of petal suffused with La France Pink, Plate 1. Reverse of petals—La France Pink, Plate 1, overcast with Cameo Pink, Plate 26. General tonality from a distance—Eosine Pink, Plate 1.

*Discoloration.*—General tonality at end of first day—Eosine Pink, Plate 1. Second day—Eosine Pink, Plate 1, lightly overcast with La France Pink, Plate 1. Third day—Eosine Pink, Plate 1, overcast with La France Pink, Plate 1.

Petals:

*Texture.*—Thick; is not affected by wet or hot weather.

*Appearance.* — Inside — satiny; outside—shiny.

*Form.*—Oval, pointed.

*Arrangement.* — Imbricated (regularly arranged shingle-like).

*Petaloids in center.*—Few; small.

*Persistence.*—Drop off cleanly.

*Fragrance.*—Moderate. Nature—tea (average hybrid tea scent).

*Lasting quality.*—On the plant—long. As cut flower—long.

*Genital organs*

Stamens, anthers: Small; few; arranged regularly around styles. Color—Cadmium Yellow, Plate 3.

Stamens, filaments (threads): Medium length. Color—Baryta Yellow, Plate 4.

Pollen: Color—Cream Color, Plate 16.

Styles: Loosely separated; uneven length; medium length; thin.

Stigmas: Color—Light Green Yellow, Plate 5.

Ovaries: All enclosed in calyx.

Hips: None.

Seeds: None.

*Plant*

Form: Bush.

Growth: Vigorous; upright.

Foliage: 5 to 7 leaflets.

*Size.*—Medium.

*Quantity.*—Abundant.

*Color.*—New foliage: upper side—Oil Green, Plate 5, lightly overcast with Oxblood Red, Plate 1; under side—Yellowish Oil Green, Plate 5, lightly overcast with Oxblood Red, Plate 1. Old foliage: upper side—Forest Green, Plate 17; under side—Bice Green, Plate 17.

*Shape.*—Oval-pointed.

*Texture.* — Upper side — leathery; glossy. Under side—rough.

*Ribs and veins.*—Ordinary.

*Edge.*—Serrated (saw-toothed).

*Serration.*—Single; small.

*Leaf stem.*—Color—Cress Green, Plate 31. Under side—prickles.

*Stipules.*—Medium length; bearded.

Wood:

*New wood.*—Color—Scheele's Green, Plate 6. Bark—smooth.

*Old wood.*—Color—Cress Green, Plate 31. Bark—smooth.

Thorns:

*Thorns.*—Quantity—on main stalks from base and on laterals from stalk—ordinary. Form—narrow base; medium length; some straight and some hooked downward. Color when young—Carmine, Plate 1. Position—irregular.

*Prickles.*—On main stalks and on laterals—none.

*Short needles*—On main stalks and on laterals—none.

I claim:

A new and distinct variety of rose plant of the large-flowered polyantha class, substantially as herein shown and described, characterized particularly as to novelty by its type of plant growth and type of flowers comparable to those of "Pinocchio" (Plant Patent No. 484), by its relatively great floriferousness, by the Begonia Rose general color tonality of its half-open flowers, by the Eosine Pink general color tonality suffused over the lower half of the petals with La France Pink color in the fully-open flowers, and by its suitability for both outdoor planting and greenhouse culture.

No references cited.